United States Patent
Ahmed et al.

(10) Patent No.: US 9,770,225 B2
(45) Date of Patent: *Sep. 26, 2017

(54) COMBINATION SENSOR GUIDEWIRE AND METHODS OF USE

(71) Applicant: Volcano Corporation, San Diego, CA (US)

(72) Inventors: Masood Ahmed, Rocklin, CA (US); Edward Anthony Oliver, Folsom, CA (US); Joseph Puleo, Pollock Pines, CA (US); Christopher Dee Ingman, Pollock Pines, CA (US); Blair D. Walker, Mission Viejo, CA (US)

(73) Assignee: Volcano Corporation, San Diego, CA (US)

( * ) Notice: Subject to any disclaimer, the term of this patent is extended or adjusted under 35 U.S.C. 154(b) by 1283 days.

This patent is subject to a terminal disclaimer.

(21) Appl. No.: 13/632,878

(22) Filed: Oct. 1, 2012

(65) Prior Publication Data

US 2013/0030300 A1    Jan. 31, 2013

Related U.S. Application Data

(63) Continuation of application No. 11/236,318, filed on Sep. 26, 2005, now Pat. No. 8,277,386.
(Continued)

(51) Int. Cl.
*A61B 5/0215* (2006.01)
*A61B 8/06* (2006.01)
(Continued)

(52) U.S. Cl.
CPC ............ *A61B 8/06* (2013.01); *A61B 5/02158* (2013.01); *A61B 8/12* (2013.01); *A61B 8/445* (2013.01);
(Continued)

(58) Field of Classification Search
CPC ......... A61B 5/02158; A61B 8/06; A61B 8/12; A61B 8/445; A61B 2562/0247
(Continued)

(56) References Cited

U.S. PATENT DOCUMENTS

| 3,724,274 A | 4/1973 | Millar |
| 4,274,423 A | 6/1981 | Mizuno |

(Continued)

FOREIGN PATENT DOCUMENTS

| JP | 4017843 | 1/1992 |
| JP | 7148123 | 6/1995 |
| JP | 10505269 | 5/1998 |

OTHER PUBLICATIONS

European Patent Office, European Search Report and Opinion issued Jun. 9, 2010, Application No. 05800066.2-2319/1804675 PCT/US2005034959, 10 pages.
(Continued)

*Primary Examiner* — Navin Natnithithadha

(57) ABSTRACT

The present invention provides for an improved combination sensor tip that includes an ultrasound transducer and a pressure sensor both disposed at or in close proximity to the distal end of the combination sensor tip. The present invention also provides for an improved connector to couple a guide wire to a physiology monitor that reduces torsional resistance when maneuvering the guide wire.

19 Claims, 17 Drawing Sheets

Related U.S. Application Data

(60) Provisional application No. 60/613,847, filed on Sep. 27, 2004.

(51) Int. Cl.
*A61B 8/12* (2006.01)
*A61B 8/00* (2006.01)

(52) U.S. Cl.
CPC ..... *A61B 5/0215* (2013.01); *A61B 2562/0247* (2013.01)

(58) Field of Classification Search
USPC ......... 600/481, 483–486, 488, 500–506, 549
See application file for complete search history.

(56) References Cited

U.S. PATENT DOCUMENTS

| | | | |
|---|---|---|---|
| 4,554,927 A | 11/1985 | Fussell | |
| 4,610,256 A | 9/1986 | Wallace | |
| 4,722,348 A | 2/1988 | Ligtenberg | |
| 4,733,669 A | 3/1988 | Segal | |
| 4,771,782 A | 9/1988 | Millar | |
| 4,771,788 A | 9/1988 | Millar | |
| 4,815,472 A | 3/1989 | Wise | |
| 4,881,410 A | 11/1989 | Wise | |
| 4,901,731 A | 2/1990 | Millar | |
| 4,901,735 A | 2/1990 | Von Berg | |
| 4,920,967 A | 5/1990 | Cottonaro | |
| 4,928,693 A | 5/1990 | Goodin | |
| 4,953,553 A | 9/1990 | Tremulis | |
| 4,964,409 A | 10/1990 | Tremulis | |
| 4,967,753 A | 11/1990 | Haase et al. | 600/468 |
| 4,991,588 A | 2/1991 | Pflueger | |
| 5,013,396 A | 5/1991 | Wise | |
| 5,046,497 A | 9/1991 | Millar | |
| 5,050,297 A | 9/1991 | Metzger | |
| 5,059,851 A | 10/1991 | Corl | |
| 5,067,491 A * | 11/1991 | Taylor, II | A61B 5/0215 600/486 |
| 5,085,223 A | 2/1992 | Lars | |
| 5,113,868 A | 5/1992 | Wise | |
| 5,125,137 A | 6/1992 | Corl | |
| 5,163,445 A | 11/1992 | Christian | |
| 5,178,153 A | 1/1993 | Einzig | |
| 5,178,159 A | 1/1993 | Christian | |
| 5,207,102 A * | 5/1993 | Takahashi | G01L 19/0084 29/621.1 |
| 5,207,103 A | 5/1993 | Wise | |
| 5,220,924 A | 6/1993 | Frazin | |
| 5,226,421 A | 7/1993 | Frisbie | |
| 5,226,423 A | 7/1993 | Tenerz | |
| 5,313,957 A | 5/1994 | Little | |
| 5,348,481 A * | 9/1994 | Ortiz | H01R 24/58 439/25 |
| 5,358,409 A * | 10/1994 | Obara | A61N 1/02 439/20 |
| 5,412,994 A | 5/1995 | Cook | |
| 5,450,091 A | 9/1995 | Hama | |
| 5,450,853 A | 9/1995 | Hastings | |
| 5,581,144 A | 12/1996 | Corl | |
| 5,715,827 A | 2/1998 | Corl | |
| 5,771,902 A | 6/1998 | Lee et al. | 128/897 |
| 5,796,044 A | 8/1998 | Cobian et al. | 174/103 |
| 5,873,835 A | 2/1999 | Hastings et al. | |
| 5,902,248 A | 5/1999 | Millar et al. | 600/485 |
| 5,935,159 A | 8/1999 | Cross et al. | 607/116 |
| 5,964,714 A | 10/1999 | Lafontaine | |
| 5,997,487 A | 12/1999 | Kolehmainen et al. | 600/585 |
| 6,018,684 A | 1/2000 | Bartig et al. | 607/122 |
| 6,089,103 A | 7/2000 | Smith | |
| 6,106,476 A | 8/2000 | Corl | |
| 6,112,598 A | 9/2000 | Tenerz | |
| 6,142,958 A | 11/2000 | Hammarstrom | |
| 6,167,763 B1 | 1/2001 | Tenerz | |
| 6,181,971 B1 | 1/2001 | Doan | 607/116 |
| 6,249,708 B1 | 6/2001 | Nelson et al. | 607/122 |
| 6,253,111 B1 | 6/2001 | Carner | 607/122 |
| 6,409,677 B1 | 6/2002 | Tulkki | |
| 6,471,656 B1 | 10/2002 | Shalman et al. | |
| 6,517,481 B2 | 2/2003 | Hoek | |
| 6,551,250 B2 | 4/2003 | Khalil | |
| 6,615,667 B2 | 9/2003 | Smith | |
| 6,672,172 B2 | 1/2004 | Tulkki | |
| 6,767,327 B1 | 7/2004 | Corl et al. | |
| 6,926,674 B2 | 8/2005 | Tenerz | |
| 6,976,965 B2 | 12/2005 | Corl et al. | 600/486 |
| 7,097,620 B2 | 8/2006 | Corl et al. | 600/486 |
| 7,120,502 B2 | 10/2006 | Tuominen | 607/119 |
| 7,130,700 B2 | 10/2006 | Gardeski et al. | 607/122 |
| 7,186,234 B2 | 3/2007 | Dahla et al. | 604/22 |
| 7,270,661 B2 | 9/2007 | Dahla et al. | 606/41 |
| 7,322,960 B2 | 1/2008 | Yamamoto et al. | 604/117 |
| 7,395,116 B2 | 7/2008 | Mehdizadeh et al. | 607/37 |
| 7,555,349 B2 * | 6/2009 | Wessman | A61N 1/0551 607/116 |
| 7,641,757 B2 * | 1/2010 | Kampa | A61M 25/0012 156/244.13 |
| 7,824,517 B2 * | 11/2010 | Kampa | A61M 25/0012 156/244.13 |
| 7,877,151 B2 | 1/2011 | Wengreen et al. | 607/122 |
| 7,877,869 B2 * | 2/2011 | Mehdizadeh | A61N 1/056 29/592.1 |
| 7,891,085 B1 * | 2/2011 | Kuzma | A61N 1/0551 29/825 |
| 7,914,520 B2 * | 3/2011 | Kennedy, II | A61M 25/00 604/534 |
| 8,231,537 B2 * | 7/2012 | Ahmed | A61B 5/02158 600/485 |
| 8,277,386 B2 * | 10/2012 | Ahmed | A61B 5/02158 600/486 |
| 2002/0059827 A1 | 5/2002 | Smith | |
| 2002/0095151 A1 * | 7/2002 | Dahla | A61B 18/148 606/41 |
| 2002/0099366 A1 * | 7/2002 | Dahla | A61B 18/148 606/41 |
| 2003/0018273 A1 | 1/2003 | Corl et al. | 600/486 |
| 2003/0040674 A1 * | 2/2003 | Corl | A61B 5/0215 600/486 |
| 2004/0249295 A1 * | 12/2004 | Ueno | A61N 1/056 600/509 |
| 2004/0260241 A1 * | 12/2004 | Yamamoto | A61N 1/0575 604/117 |
| 2005/0054905 A1 * | 3/2005 | Corl | A61B 5/14539 600/309 |
| 2006/0074318 A1 | 4/2006 | Ahmed et al. | 600/465 |
| 2006/0241505 A1 | 10/2006 | Ahmed et al. | 600/486 |
| 2013/0030300 A1 * | 1/2013 | Ahmed | A61B 5/02158 600/454 |
| 2013/0030303 A1 * | 1/2013 | Ahmed | A61B 5/02158 600/465 |

OTHER PUBLICATIONS

International Search Report for PCT/US05/34959, dated Apr. 10, 2007.
Written Opinion for PCT/US05/34959, dated Apr. 10, 2007.
Barbato, E., Aarnoudse, W., Aengevaeren, W., Werner, G., Klauss, V., Bojara, W., Herzfeld, I., Oldroyd, K., Pijls, N., De Bruyne, B., "Validation of Coronary Flow Reserve Measurements by Thermodilution in Clinical Practice," European Heart Journal, 2004, pp. 219-223, vol. 25, No. 3, Elsevier Ltd, Amsterdam, The Netherlands.
Chau, H-L., Wise, K.D., "An Ultraminiature Solid-State Pressure Sensor for a Cardiovascular Catheter," IEEE Transactions on Electron Devices, 1988, pp. 2355-2362, vol. 35, No. 12, Institute of Electrical and Electronics Engineers, New York, U.S.A.
Chau, H-L., Wise, K.D., "An Ultraminiature Solid-State Pressure Sensor for a Cardiovascular Catheter 1987, Transducers," pp. 344-347, 1987, Transducers '87.

(56) References Cited

OTHER PUBLICATIONS

De Bruyne, B., Pijls, N., Smith, L., Wievegg, M., Heyndrickx, G., "Coronary Thermodilution to Assess Flow Reserve: Experimental Validation," Circulation, 2001, pp. 2003-2006, vol. 104, No. 17, American Heart Association, Dallas, U.S.A.

Fearon, W., Aarnoudse, W., Pijls, N., De Bruyne, B., Balsam, L., Cooke, D., Robbins, R., Fitzgerald, P., Yeung, A., Yock, P., "Microvascular Resistance Is Not Influenced by Epicardial Coronary Artery Stenosis Severity: Experimental Validation," Circulation 2004, pp. 2269-2272, vol. 109, No. 19, American Heart Association, Dallas, U.S.A.

Fearon, W., Farouque, H.M., Balsam, L., Cooke, D., Robbins, R., Fitzgerald, P., Yeung, A., Yock, P., "Comparison of Coronary Thermodilution and Doppler Velocity for Assessing Coronary Flow Reserve," Circulation, 2003, pp. 2198-2200, vol. 108, No. 25, American Heart Association, Dallas, U.S.A.

Fearon, W., Nakamura, M., Lee, D., Rezaee, M., Vagelos, R., Hunt, S., Fitzgerald, P., Yock, P., Yeung, A., "Simultaneous Assessment of Fractional and Coronary Flow Reserves in Cardiac Transplant Recipients: Physiologic Investigation for Transplant Arteriopathy (PITA Study)," Circulation, 2003, pp. 1605-1610, vol. 108, No. 13, American Heart Association, Dallas, U.S.A.

Pijls, N., De Bruyne, B., Smith, L., Aarnoudse, W., Barbato, E., Bartunek, J., Bech., G., Van De Vosse, F., "Coronary Thermodilution to Assess Flow Reserve: Validation in Humans," Circulation, 2002, pp. 2482-2486, vol. 105, No. 21, American Heart Association, Dallas, U.S.A.

Neishi et al., "Measurement of Coronary Flow Reserve by Pressure/Temperature Sensor Guide Wire-Based Thermodilution in Experimental Models," J. Cardiol. Dec. 2002; 40(6): 249-257.

Shindo et al., "Measurement of Fractional and Coronary Flow Reserve Using Dual Sensor Guide Wire," J. Cardiol. Nov. 2002; 40(5): 189-197.

Siebes, et al., "Single-Wire Pressure and Flow Velocity Measurement to Quantify Coronary Stenosis Hemodynamics and Effects of Percutaneous Interventions," Circulation, Feb. 17, 2004, 756-762.

* cited by examiner

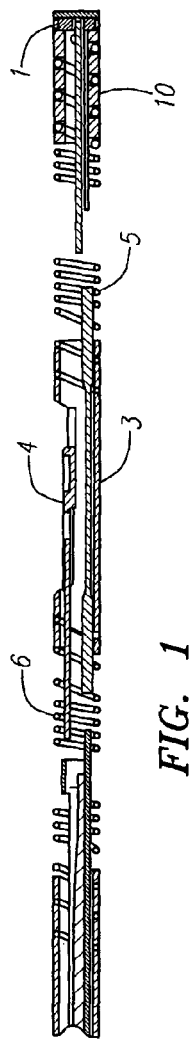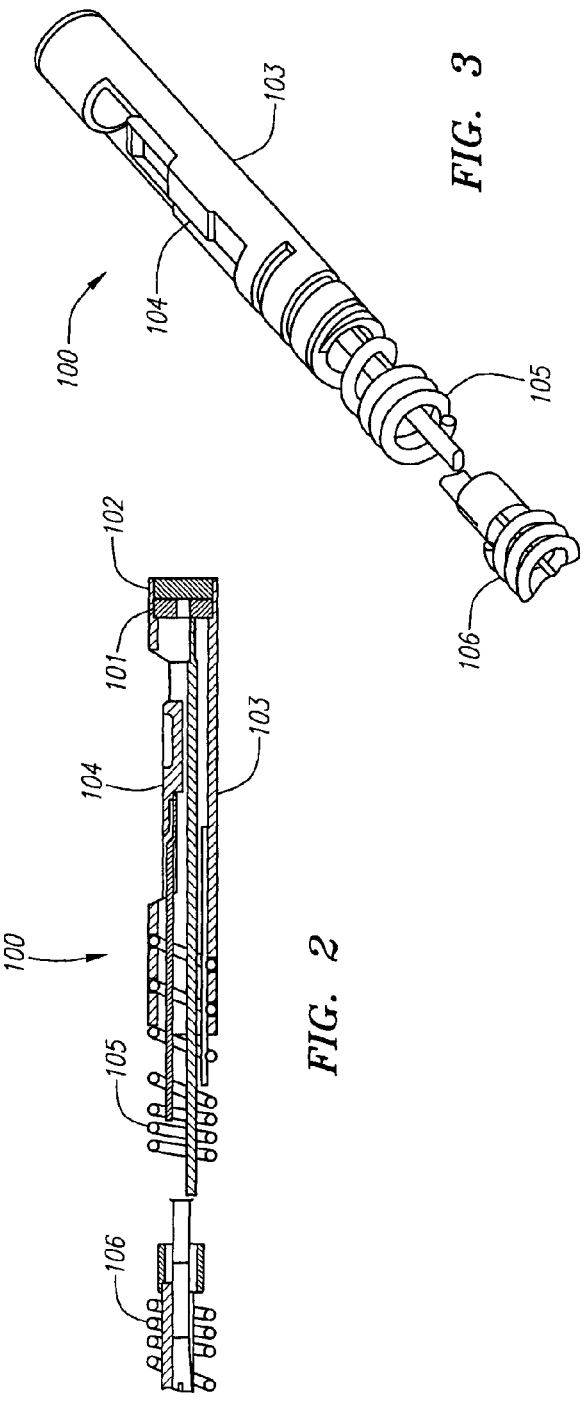
FIG. 1
FIG. 2
FIG. 3

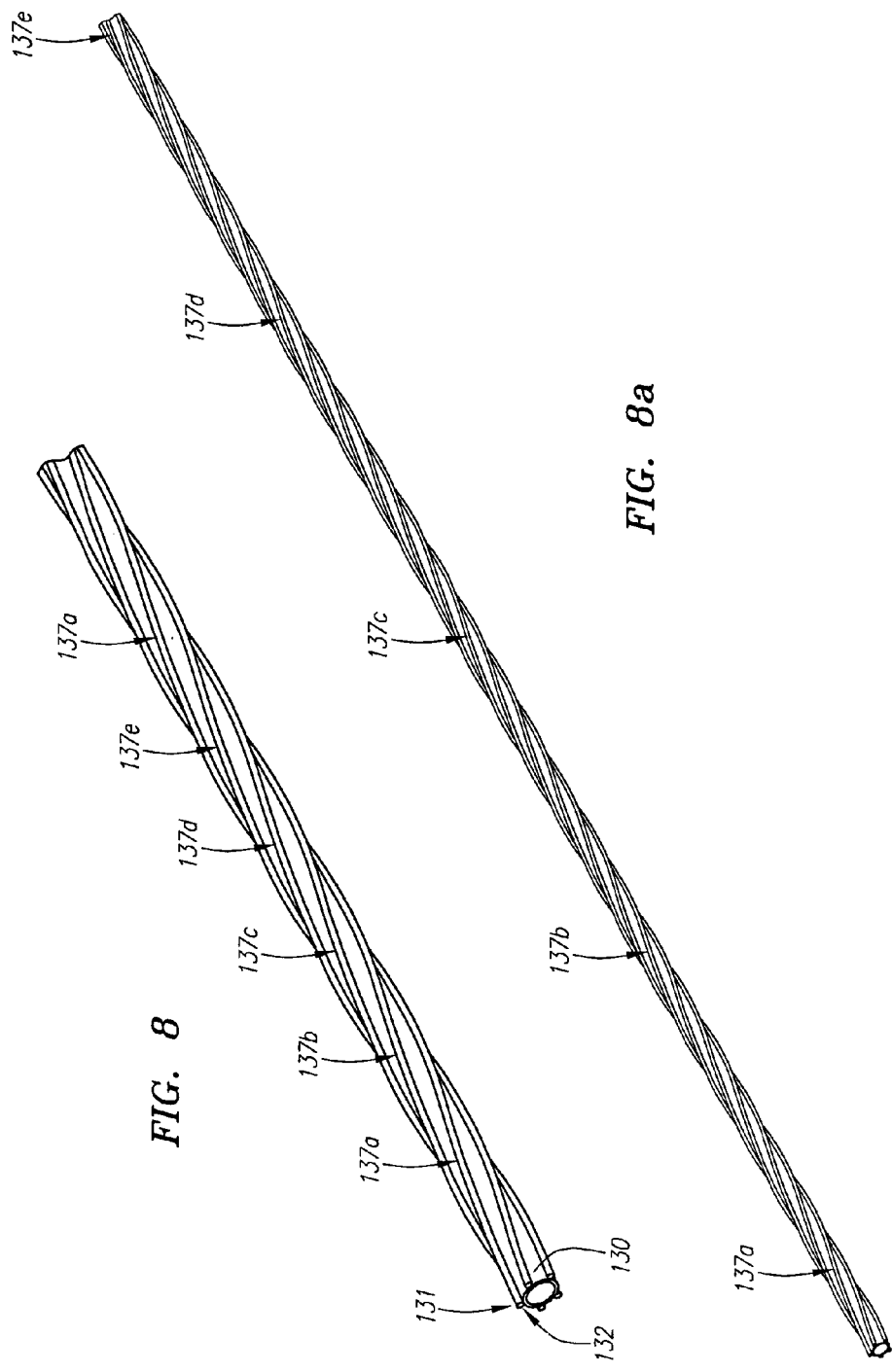

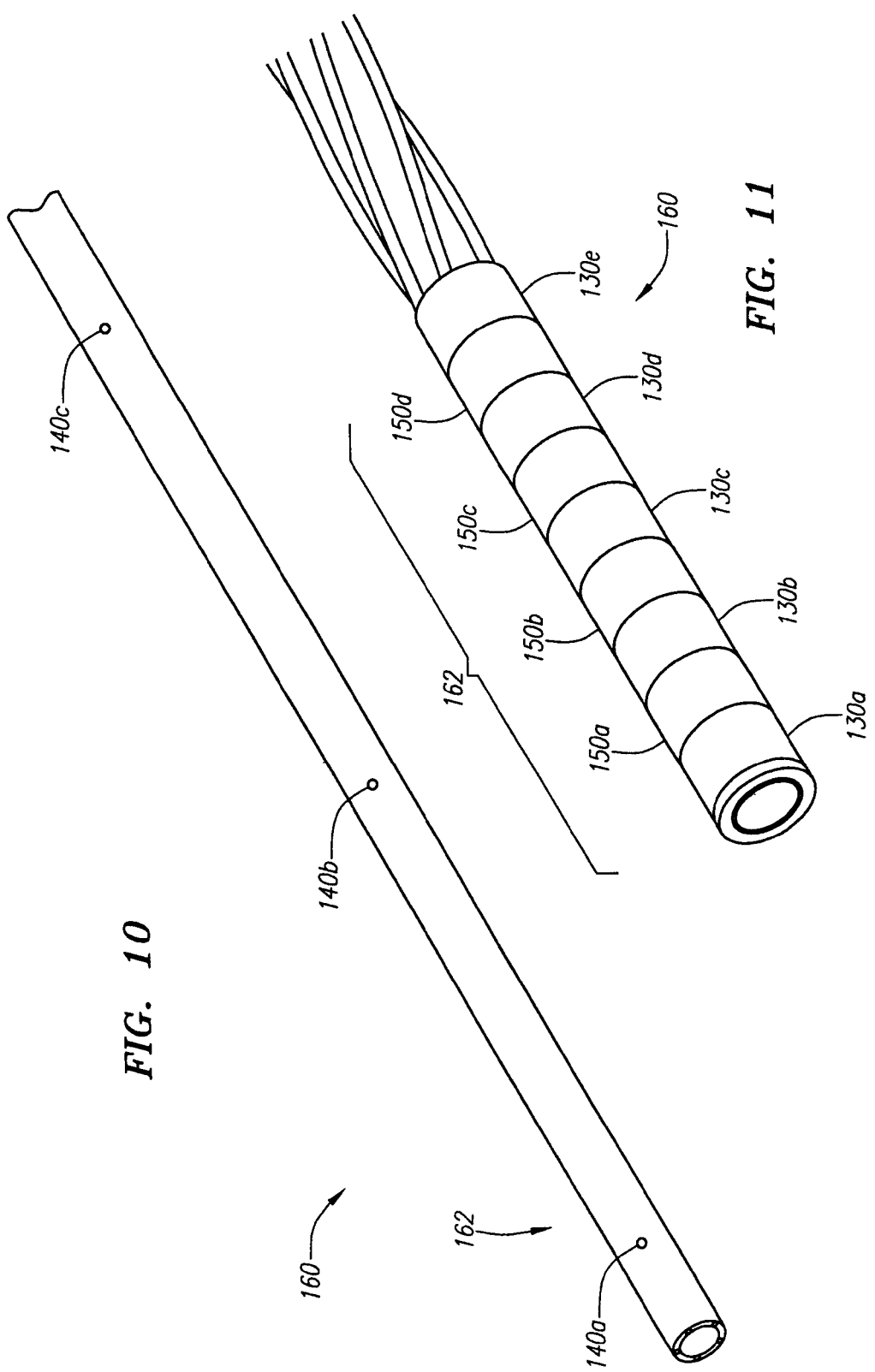

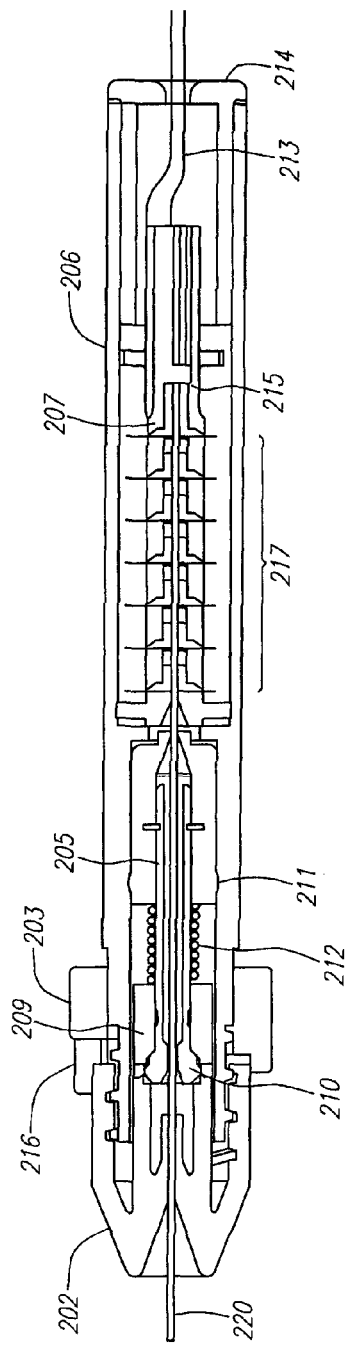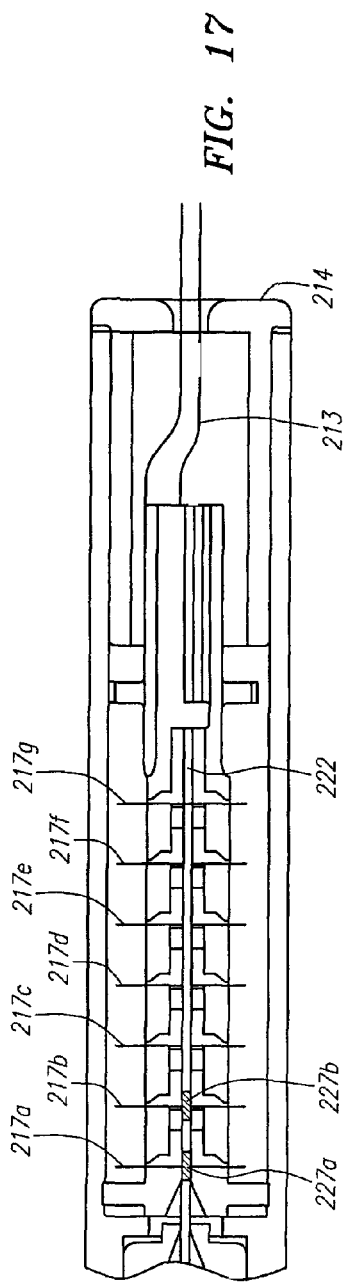

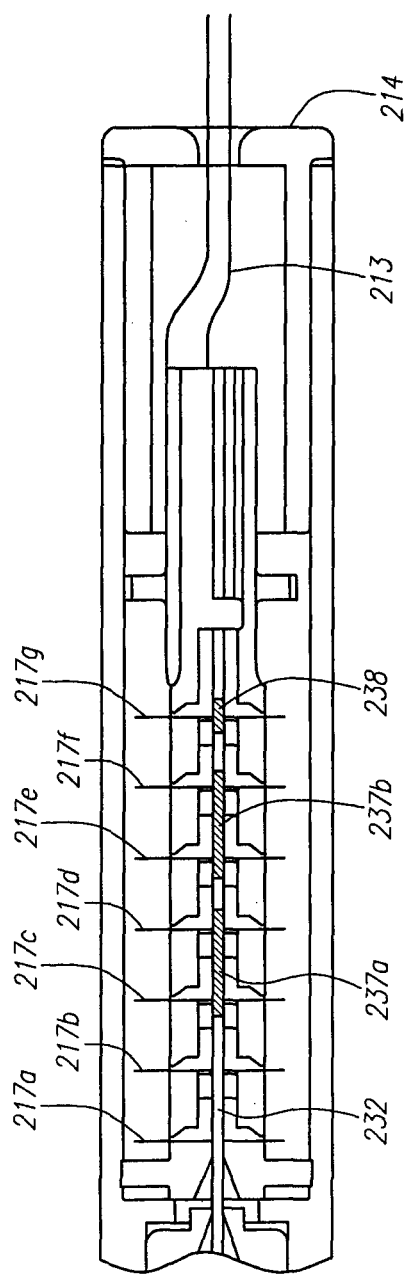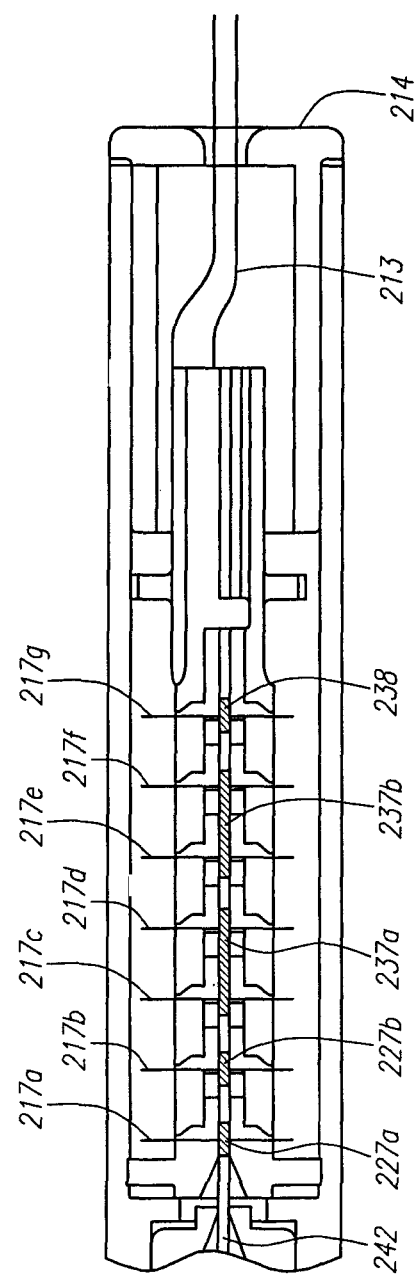

COMBINATION SENSOR GUIDEWIRE AND METHODS OF USE

RELATED APPLICATIONS

This application is a continuation of U.S. patent application Ser. No. 11/236,318, filed on Sep. 26, 2005, which claims the benefit of U.S. provisional patent application Ser. No. 60/613,847, entitled Improved Connector and Combined Miniature Pressure and Flow Sensor, filed Sep. 27, 2004, each of which is incorporated herein by reference in its entirety for all purposes.

FIELD OF THE INVENTION

This invention relates to an ultra miniature combined pressure sensor and flow sensor, an apparatus using the same, and methods for using the same. This invention also relates to an improved connector for connecting a guide wire to a monitor. This invention is particularly suitable for making pressure measurements in coronary arteries of human beings.

BACKGROUND

It has been well known that it is desirable to make pressure measurements in vessels and particularly in coronary arteries with the advent of angioplasty. Typically in the past, such pressure measurements have been made by measuring the pressure at a proximal extremity of a lumen provided in a catheter advanced into the coronary artery of interest. Such an approach has, however, been less efficacious as the diameters of the catheters became smaller with the need to advance the catheter into smaller vessels and to the distal side of atherosclerotic lesions. This made necessary the use of smaller lumens that gave less accurate pressure measurements and in the smallest catheters necessitated the elimination of such a pressure lumen entirely. Furthermore, the catheter is large enough to significantly interfere with the blood flow and damp the pressure resulting in an inaccurate pressure measurement. In an attempt to overcome these difficulties, ultra miniature pressure sensors have been proposed for use on the distal extremities of a guidewire. Using a guidewire with a smaller diameter is less disruptive to the blood flow and thus provides an accurate pressure reading. Currently, the use of two sensors on the distal region of a guide wire has been proposed, such as, e.g., the use of flow sensor, for example, an ultrasound transducer or Doppler flow sensor, disposed near the distal tip of the guide wire in conjunction with a pressure sensor located proximally from the ultrasound transducer.

The current designs require a separation between the ultrasound transducer and the pressure sensor, which for some designs may be approximately 3 cm. As a result, the current designs do not allow a user to take both Doppler flow measurements using the ultrasound transducer and pressure measurements using the pressure sensor at substantially the same time at the same location, or to take both measurements near the distal tip of the guide wire. For example, because the pressure sensor is located proximal from the ultrasound transducer, the currently proposed designs require a user to advance the guide wire to a desired location, obtain a Doppler flow measurement with the ultrasound transducer, and then advance the guide wire further distally in order to obtain a pressure measurement using the pressure sensor at the same location. The additional distal movement of the guide wire using the current designs is undesirable as such movement may inflict trauma (or further trauma) to the body, such as, e.g., to the arterial walls. Another disadvantage of the separated placement of the ultrasound transducer and the pressure sensor on currently proposed designs is that there may be a limit as to how far distally a measurement may be taken with the guide wire. For example, the currently proposed designs are not able to take a measurement at the extreme distal end of a cavity or body lumen because there is no room to maneuver the pressure sensor distally to the desired location once the distal end of the guide wire is in physical contact with the distal end of the body lumen. Also, when attempting to advance one sensor to the location at which a measurement was already taken with the other sensor, it is difficult to know the exact location to stop the advancement. It has not, however, been feasible prior to the present invention to provide for two different sensors, such as, e.g., both an ultrasound transducer and a pressure sensor, in close proximity to each other near the distal tip of a guide wire. There is therefore a need for a new and improved ultra miniature pressure and flow sensor, as well as a guide wire and apparatus for utilizing the same.

In order to provide measurement data to a user, the guide wire must be coupled to a physiology monitor located at the user's end. Unfortunately, the current methods for coupling and decoupling the guide wire directly to the physiology monitor or to a cable leading to the physiology monitor are deficient in certain respects.

For example, the guide wire comprises basically a core wire and a plurality of electrical conductors disposed within an elongate tubular member for transferring electrical signals from the sensors located at the distal end of the guide wire. Usually three electrical conductors are necessary for a stand alone pressure measurement guidewire and two electrical conductors are necessary for a stand alone flow sensor guidewire, thus in a combination guide pressure and flow measurement guidewire, five electrical conductors are required. These electrical conductors extend through the lumen from the pressure and flow sensors at the distal end of the tubular member to a male connector located at the proximal end of the guidewire for electrically and mechanically connecting to a female connector, for example on a physiology monitor or a cable. During connection, there is a substantial risk that the proximal end of the guidewire and/or male connector may be bent and the electrical connections may be damaged. Thus it is desired that the proximal portion of the guidewire is as stiff as possible for pushability, handling, kink resistance and catheter support. It is also desirable that the male connector portion is as stiff as possible to aid in the attachment and detachment of the male connector to the female connector/cable. In traditional guide wires, the electrical conductors extend in the space between a stainless steel core wire and the outer elongate tubular member, usually stainless steel. The stiffness of the guidewire is due for the most part to the dimensional and material properties of the core wire and the tubular member, specifically diameter and thickness of the core wire and tubular walls. However, these properties are limited by the need to electrically insulate the electrical conductors and to ensure that the electrical conductors have enough space to freely extend without damage. The use of five electrical conductors in a combination pressure and flow sensor guidewire, instead of the traditional two or three conductors for stand alone flow or pressure sensor guidewires, further complicates the solution.

Additionally, the use of traditional rotary connectors to connect the guidewire to the physiology monitor may render the guide wire awkward to manipulate and often require high insertion forces to place the guide wire in the connector. These traditional connectors also exhibit a high degree of torsional resistance, which also increases the difficulty of manipulating the guide wire within the body.

In general it is an object of the present invention to provide an ultra miniature pressure sensor, ultrasound transducer and guide wire and apparatus utilizing the same, making possible pressure and velocity measurements using a pressure sensor and an ultrasound transducer located in close proximity to each other on or near the distal end of the guide wire.

Another object of the present invention is to provide for increased stiffness in the proximal end of the guidewire to increase the catheter support, handling, kink resistance and pushability of the guidewire and decrease the risk of bending the proximal end of the guidewire or damaging the electrical connectors inside of the guidewire.

Another object of the present invention is to provide for improved methods for coupling a guide wire to a physiology monitor or cable that increase the ease of connecting the guide wire to the monitor as well as increase the ease of manipulating the guide wire within the body.

Additional features and objects of the invention will appear from the following description in which the preferred embodiments are set forth in detail in conjunction with the accompanying drawings.

SUMMARY OF THE INVENTION

The present invention provides for combination sensor tip which may be secured to the distal end of a guidewire having an ultra miniature pressure sensor and an ultrasound transducer mounted on or near the distal end of the combination sensor housing. In this embodiment, the pressure sensor and the ultrasound transducer are mounted in close proximity to one another in order to enable pressure and flow velocity measurements to be taken at substantially the same time and location, and thus ensure a greater accuracy and consistency in the measurements. For example, the proximity of the pressure and flow sensors minimizes the effect of side branch steal which can cause hemodynamic changes over short segments. The close proximity of the sensors also increases the placement accuracy of the sensors. Finally, the distal placement of the pressure sensor and ultrasound transducer on the combination tip increases how far the sensors may be advanced within the body.

The present invention also provides for a guidewire with an increased tubular wall thickness and a larger diameter core wire. This embodiment provides improved stiffness in the proximal section of the guidewire, making it more durable and resistant to kinking, while maintaining the ability to insulate the electrical conductors and permitting them to freely extend from the pressure sensor and ultrasound transducer inside the guidewire without damage. In one embodiment, this increased stiffness, is achieved by using an elongate tubular member with a thickened wall containing a groove for each electrical conductor extending the length of the tubular member. The electrical conductors may then be positioned in the grooves where they will still have space to freely extend the length of the cable. Since the conductors are resting partially inside the grooves, the thickness of the tubular member walls may be increased without cutting onto the free space for the electrical conductors. In an alternative embodiment, the stiff inner core wire may also be increased in diameter to further reinforce the stiffness of the guidewire. Alternatively, the guidewire may be created out of a composite polyimide tube wherein the electrical conductor wires may be sandwiched between layers of the polyimide tube as it is being formed. In this embodiment, the diameter of the stiff inner core wire may also be increased since the wires are embedded in the polyimide tube and no longer need the space between the tubular member and the inner core wire to freely extend. Furthermore, since the electrical conductors are insulated by the polyimide layers, additional insulating material between the electrical conductors and the steel inner core wire is no longer necessary. Thus, the diameter of the inner core wire may be even further enlarged.

The present invention also provides for an improved connector to couple a guide wire to a physiology monitor. The connector includes an outer housing having an inner passage which further contains a stationary contact housing for electrically connecting to the conductors of the coupled guidewire and a rotatable bearing assembly for physically engaging the wire. In this embodiment, the bearing assembly of engages the wire and is able to freely spin while the connector housing and the contact housing remain static. This spinning capability of the bearing assembly reduces torsional resistance between the guide wire and a cable or monitor to which it is connected, thereby allowing a user to manipulate the guide wire using less torque than required with current connectors.

These and other objects and features of the present invention will be appreciated upon consideration of the following drawings and detailed description.

BRIEF DESCRIPTION OF THE FIGURES

FIG. 1 illustrates a prior art combination sensor wire.

FIG. 2 illustrates an embodiment of the combination sensor tip according to the present invention.

FIG. 3 illustrates an alternative view of a combination sensor tip according to the present invention.

FIG. 8 illustrates an embodiment of the guidewire according to the present invention.

FIG. 8a illustrates an embodiment of the guidewire according to the present invention.

FIG. 10 illustrates a proximal end of an alternative embodiment of the guidewire according to the present invention.

FIG. 11 illustrates a proximal end of an alternative embodiment of the guidewire according to the present invention.

FIG. 16 illustrates an embodiment of the connector of the present invention with the guidewire inserted.

FIG. 17 illustrates an embodiment of the flow guidewire contacts on the contact housing according to the present invention FIG. 18 illustrates an embodiment of the pressure guidewire contacts on the contact housing according to the present invention FIG. 19 illustrates an embodiment of the pressure and flow guidewire contacts on the contact housing according to the present invention

DETAILED DESCRIPTION

Figure 4:
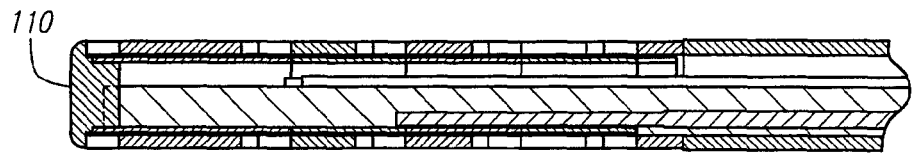
FIG. 4 illustrates the connectors of the combination tip guidewire according to the present invention.

Turning to FIGS. 2-3, a combination sensor tip 100 of the present invention is illustrated. The combination sensor tip 100 includes a flow sensor 101, for example an ultrasound transducer, a Doppler flow sensor or any other suitable flow sensor, disposed at or in close proximity to the distal end 102 of the combination sensor tip 100. The ultrasound transducer 101 may be any suitable transducer, and may be mounted in the distal end using any conventional method, including the manner described in U.S. Pat. No. 5,125,137, which is fully incorporated herein by reference. Conductors (not shown) may be secured to the front and rear sides of the ultrasound transducer 101, and the conductors may extend interiorly to the proximal extremity of a guide wire.

The combination sensor tip 100 also includes a pressure sensor 104 also disposed at or in close proximity to the distal end 102 of the combination sensor tip 100. The pressure sensor 104 may be of the type described in U.S. Pat. No. 6,106,476, which is fully incorporated herein by reference. For example, the pressure sensor 104 may be comprised of a crystal semiconductor material having a recess therein and forming a diaphragm bordered by a rim. A reinforcing member may be bonded to the crystal to reinforce the rim of the crystal, and may have a cavity therein underlying the diaphragm and exposed to the diaphragm. A resistor having opposite ends may be carried by the crystal and may have a portion thereof overlying a portion of the diaphragm. Leads may be connected to opposite ends of the resistor and extend proximally within the guide wire. Additional details of suitable pressure sensors that may be used as the pressure sensor 104 are described in U.S. Pat. No. 6,106,476. U.S. Pat. No. 6,106,476 also describes suitable methods for mounting the pressure sensor 104 within the combination sensor tip 100. In one embodiment, the pressure sensor 104 is oriented in a cantilevered position within a sensor housing 103. For example, the sensor housing 103 preferably includes a lumen surrounded by housing walls. When in a cantilevered position, the pressure sensor 104 projects into the lumen of the sensor housing 103 without contacting the walls of the sensor housing 103.

As depicted in FIGS. 2-3, the combination sensor tip 100 incorporates a sensor housing 103 designed to enclose both the ultrasound transducer 101 and the pressure sensor 104. One advantage of the sensor housing 103 is that because the sensor housing 103 encloses both the ultrasound transducer 101 and the pressure sensor 104, the need for two separate housings, i.e., one for an ultrasound transducer and one for a pressure sensor, is eliminated. Accordingly, the use of a common sensor housing 103 for the ultrasound transducer 101 and the pressure sensor 104 makes the combination sensor tip 100 easier to manufacture than current designs.

Additionally, unlike prior art designs, such as shown in FIG. 1, the combination sensor tip 100 of the present invention provides for both the ultrasound transducer 101 and the pressure sensor 104 to be disposed near the distal end of the combination sensor tip 100. In contrast, as shown in FIG. 1, the prior art combination wire, the pressure sensor 4 is secured in a pressure sensor housing 3 and the ultrasound transducer 1 is then located on a screw tip 10 that is mounted to a coil on the distal end of the pressure sensor housing 3. This design results in a significant separation between the pressure sensor 4 and the ultrasound transducer 1 that may be in the range of 3.0 cm. The combination sensor tip 100 of the present invention is advantageous over prior art designs because by having both the ultrasound transducer 101 and the pressure sensor 104 near its distal end, the combination sensor tip 100 is capable of being positioned further distally in a, vessel or the body than the prior art designs. Additionally, the combination sensor tip 100 of the present invention, unlike the prior art, is also able to take measurements from the ultrasound transducer 101 and the pressure 104 at approximately the same location and approximately the same time, thereby resulting in greater consistency of measurements, greater accuracy of measurements, and greater accuracy of placement within the body. Furthermore, placement of both the ultrasound transducer 101 and the pressure sensor 104 near the distal end of the combination sensor tip 100 increases overall flexibility in a guide wire that incorporates the combination sensor tip 100. For example, a prior art guide wire that includes separate sensors, with the pressure sensor being located substantially proximal from the ultrasound transducer, has a longer relatively rigid area that must be devoted to the pressure and flow sensors, i.e., the distance from the ultrasound transducer to the pressure sensor. The present invention, in contrast, substantially reduces or entirely eliminates the distance between the ultrasound transducer and the pressure sensor, thereby allowing for increased flexibility across this length.

It should be noted that in an alternative embodiment of the combination sensor tip 100 (not shown) both the ultrasound transducer 101 and the pressure sensor 104 may be offset from the distal end of the combination sensor tip 100, such as, e.g., 1.5 cm to 3.0 cm from the distal end, but still located in close proximity to each other relative to prior art designs. Thus, the aforementioned advantages over the prior art design are still achieved.

Figure 20:
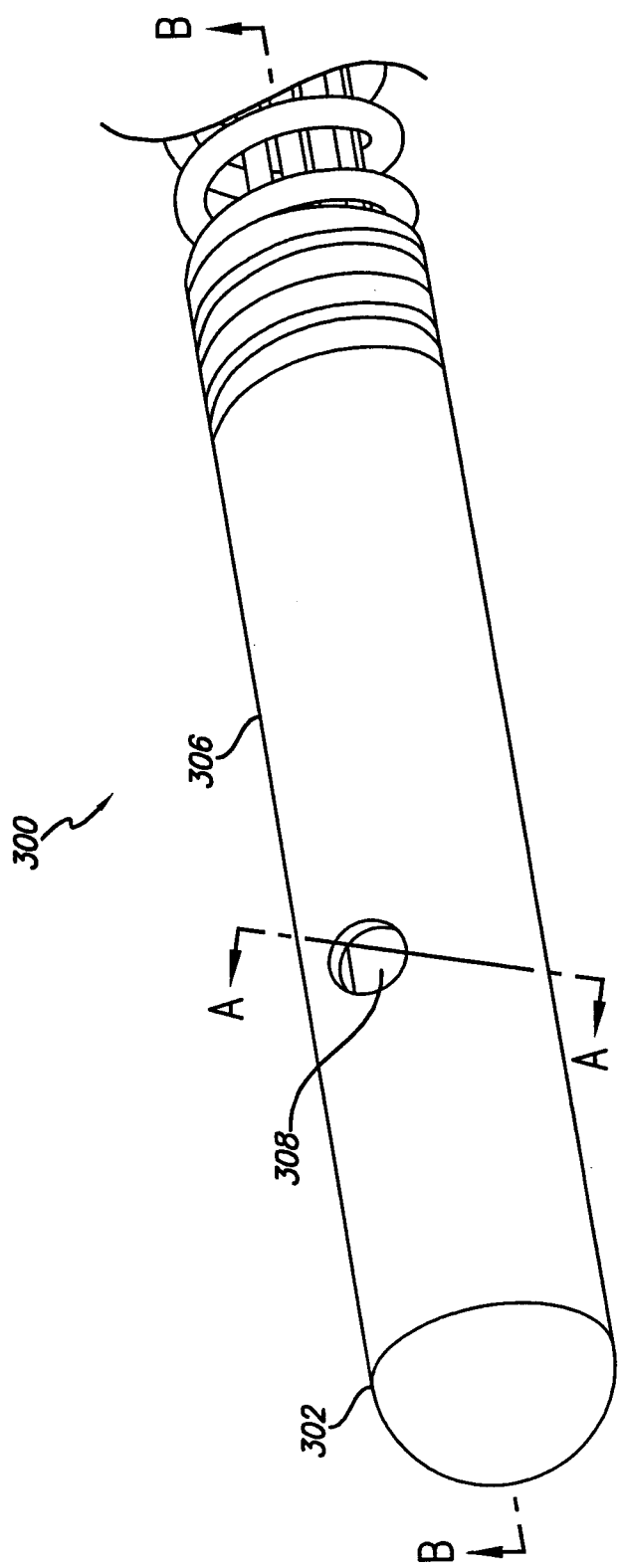
FIG. 20 illustrates an embodiment of an alternative pressure sensor housing according to the present invention.
Figure 20A:
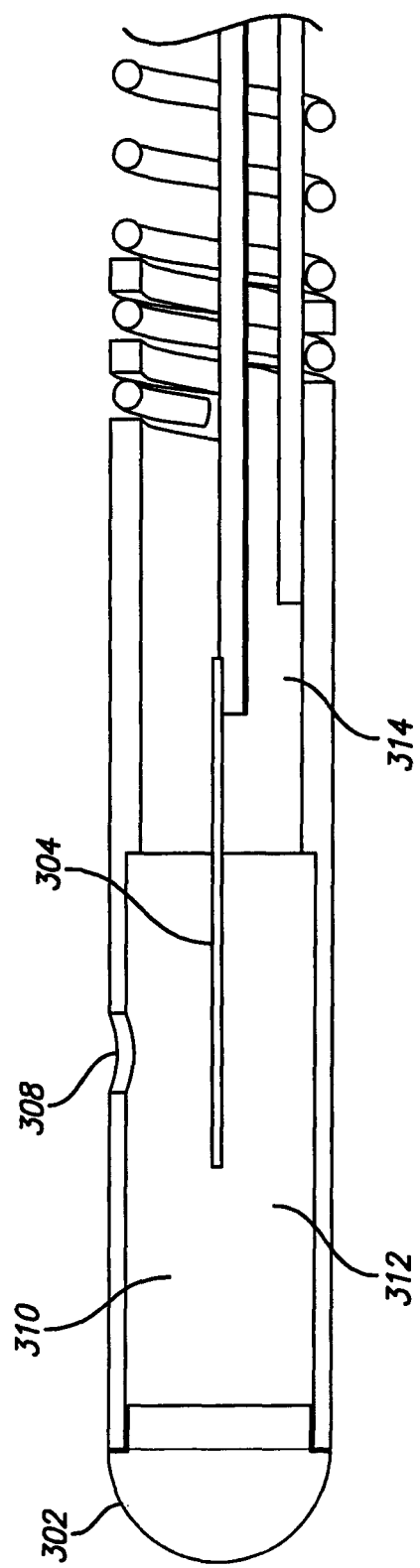
FIG. 20a illustrates a side view of longitudinal cross section of the alternative pressure sensor housing illustrated in FIG. 20 taken along the line B-B according to the present invention.
Figure 20B:
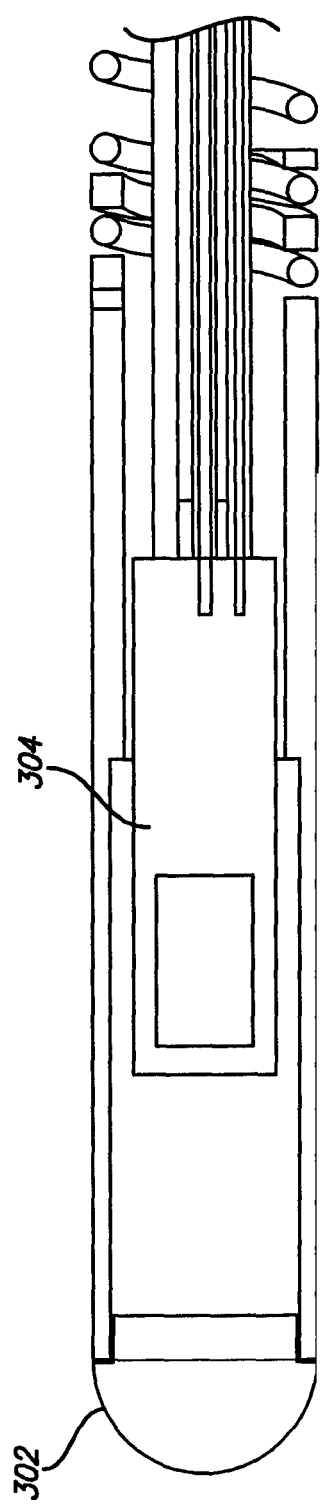
FIG. 20b illustrates a top view longitudinal cross section of an alternative pressure sensor housing illustrated in FIG. 20 taken along the line B-B according to the present invention.
Figure 20C:
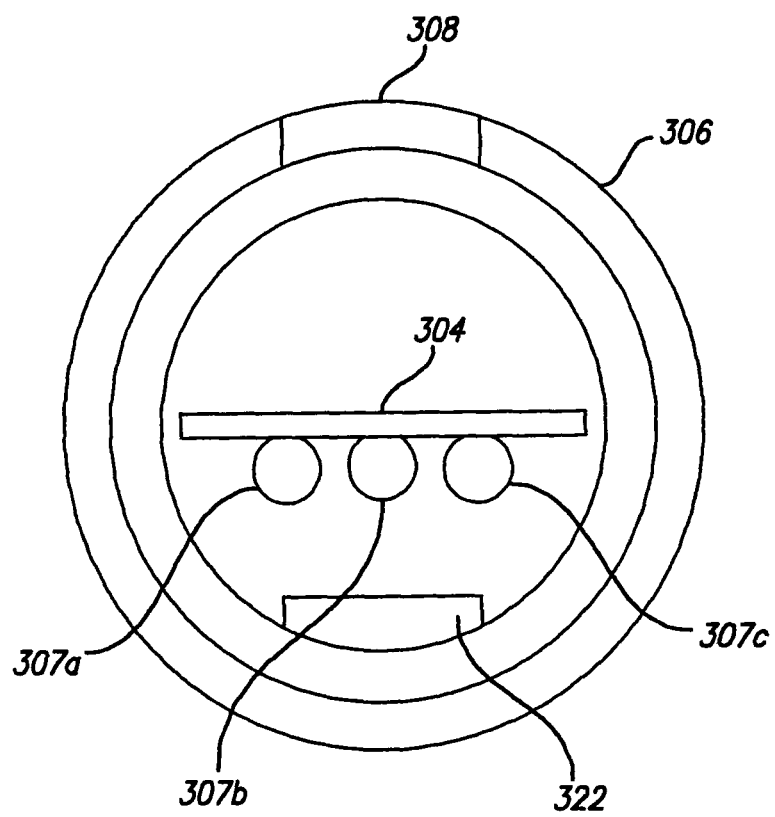
FIG. 20c illustrates a cross-section of an alternative pressure sensor housing illustrated in FIG. 20 taken along the line A-A according to the present invention.
Figure 21:
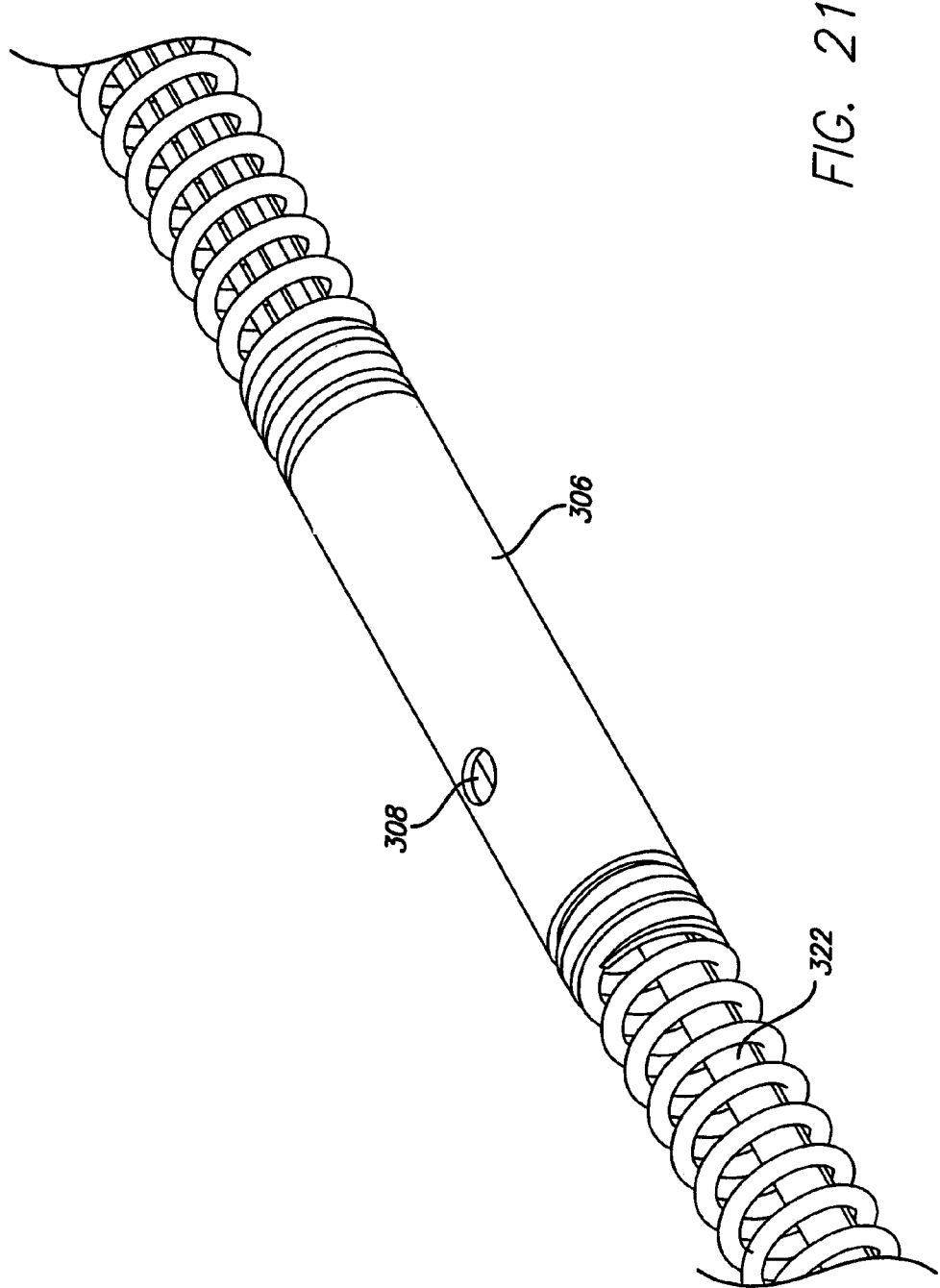
FIG. 21 illustrates an alternative pressure sensor housing according to the present invention.

In an alternative embodiment, as depicted in FIGS. 20-21, the pressure sensor housing 300 includes a tubular member 306 having an opening 308 on the outer wall in communication with the lumen and a tip 302. The tip is constructed of a solder ball. Alternatively a weld, braze, epoxy or adhesive can be used. As shown in FIG. 20a, the lumen 310 of the housing is counterbored so that the lumen 310 has a smaller inner diameter at the proximal end of the tubular member 306. For example, the housing may be constructed in the counterbore fashion with a 0.010" inner diameter at the proximal end 314 and a 0.012" inner diameter at the distal end 312. As shown in FIGS. 20a-20c, the pressure transducer 304 is coaxially housed in the lumen 310. In addition, a flow sensor (not shown) may be placed in the sensor tip 302 instead of the weld, braze, epoxy or adhesive to provide a combo sensor tip.

The advantage of the counter bore is that the housing is easier to make. The transducer 304 is simply slid into place in the lumen 310 and bonded (adhesive or epoxy) where the sides meet the proximal 0.010" inner diameter 314. The distal 0.012" inner diameter 312 allows enough room for the pressure sensitive section of the transducer to be free from any contact with the housing. Because of the counterbored lumen, there is no ledge that has to be made on the outer wall of the lumen, rather the pressure transducer communicates with the outside via an opening 308 in the outer wall of lumen. This protects better against the atherosclerotic plaque from entering and interfering with the pressure transducer. As shown in FIG. 20c, there is enough room for the three conductor wires 307a-c and the flattened core wire 322 on one side of the pressure transducer 304. In an alternative embodiment, shown in FIG. 21, the aforementioned pressure housing may be located between the 3 cm long platinum tip coil and the 27 cm long stainless steel coil for coupling the housing to the elongate tubular member of the guidewire. In this intermediate housing version, the flattened core wire 322 passes completely through the housing 306 and is bonded at the tip (not shown) of the platinum coil.

As further shown in FIGS. 2-3, a radiopaque tip coil 105 is provided at the proximal end of the combination sensor tip 100. The radiopaque tip coil 105 is coupled to a proximal coil 106, and the proximal coil 106 may be coupled to the elongate tubular member. Another improvement of the present invention over current designs that use separate pressure sensor and ultrasound transducer housings is that the present invention provides a smoother transition from the elongate tubular member to the combination sensor tip 100, i.e., the connection between the radiopaque tip coil 105, the proximal coil 106, and the rest of the guide wire is optimized relative to current designs. Specifically, the transition is smoother and more flexible because of the absence of the housing between the radiopaque tip coil 105 and the proximal coil 106. Current designs, such as the prior art guide wire shown in FIG. 1, generally have a tip coil 5 attached to a pressure sensor housing 3, which in turn is connected to a proximal coil 6. The present invention eliminates or greatly reduces the separation between the tip coil and the proximal coil that is required in current devices. Suitable coils for use with the present invention are described in U.S. Pat. No. 6,106,476.

Figure 5:
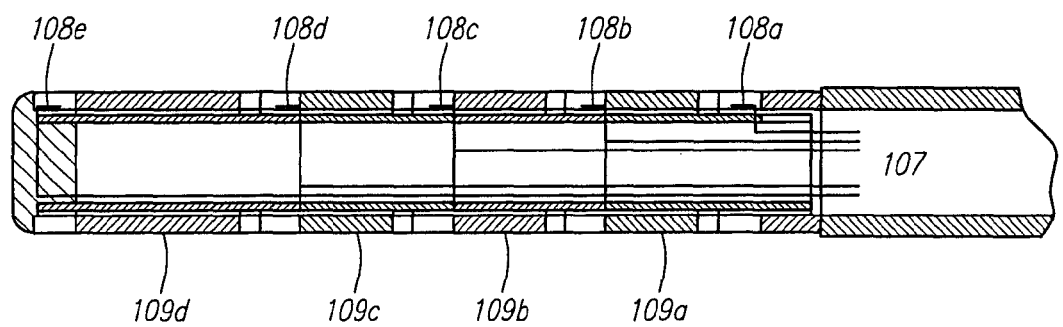
FIG. 5 illustrates an alternative view of the connectors of the combination tip guidewire according to the present invention.

As depicted in FIGS. 4-5, signals from the ultrasound transducer 101 and the pressure sensor 104 may be carried by fine wire conductors 107 passing through the guide wire to conductive bands 108a-e near the proximal end 110 of the guide wire. Usually three electrical connectors are necessary for a stand-alone pressure measurement guidewire and two electrical connectors are necessary for a stand-alone flow measurement guidewire. Thus, depicted in FIG. 4-5, a guide wire incorporating the combination sensor tip 100 of the present invention includes five electrical conductors 107 extending through the lumen of the guidewire and five conductive bands 108a-e on the proximal end 110 of the guidewire. The conductive bands 108a-e may be electrically isolated from each other by means of epoxy 109a-d. Alternatively, polyimide tubes may be used to isolate conductors from the conductive bands. The conductive bands transmit the electrical signals from the conductors via a mating connector (or contact housing as described herein with respect to a connector of the present invention) to an instrument, such as, e.g., a physiology monitor, that converts the signals into pressure and velocity readings that are displayed to the user. In addition algorithms such as Coronary Flow Reserve (CFR) and Fractional Flow Reserve (FFR) are calculated.

In general, the guide wire of the present invention is comprised of a flexible elongate element having proximal and distal ends and a diameter of 0.018" and less as disclosed in U.S. Pat. Nos. 5,125,137, 5,163,445, 5,174,295, 5,178,159, 5,226,421, 5,240,437 and 6,106,476, all of which are incorporated by reference herein.

As disclosed in the abovementioned patents, a suitable guide wire may consist of a flexible elongate element having proximal and distal extremities, and can be formed of a suitable material such as stainless steel, Nitinol, polyimide, PEEK or other metallic or polymeric materials having an outside diameter for example of 0.018" or less and having a suitable wall thickness, such as, e.g., 0.001" to 0.002". This flexible elongate element is conventionally called a hypotube. In one embodiment, the hypotube may have a length of 130 to 170 cm. Typically, such a guide wire may further include a stainless steel core wire extending from the proximal extremity to the distal extremity of the flexible elongate element to provide the desired torsional properties to facilitate steering of the guide wire in the vessel and to provide strength to the guidewire and prevent kinking.

In an alternative embodiment, for example where a smaller guide wire is desired, the guide wires disclosed in the above mentioned patents may be modified to provide for improved stiffness. For example, where a smaller guide wire is desired, the hypotube can have an exterior diameter of 0.014" or less. In such an embodiment, however, the ability to achieve a suitable stiffness of the guidewire becomes a challenge due to space constraints imposed by the both the small outer diameter of the hypotube and the restricted space in the lumen of the hypotube. The use of five electrical conductor wires required for a combination pressure and flow sensor as opposed to either two or three wires required for the individual sensor guide wires further increases the challenge.

Figure 6:
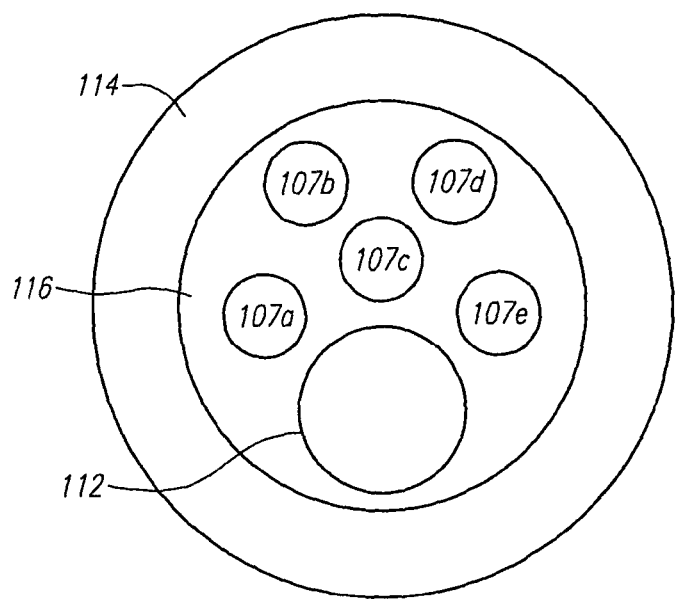
FIG. 6 illustrates a cross section of a prior art guidewire.

FIG. 6 depicts the cross-section of a typical prior art guidewire. In the prior art, the electrical conductor wires 107a-e extend in the space between the stainless steel core wire 112 and the hypotube 114. The annular space between the core wire 112 and the hypotube 114 is further filled with an electrically insulative material 116 such as epoxy or adhesive. Here, the stiffness of the guidewire is due mainly to the properties of the core wire 112 and the hypotube 114 and less so to the properties of the electrical conductors 107a-e and insulative material 116. Specifically, the stiffness of the core wire 112 is proportional to the fourth power of the diameter and the stiffness of the hypotube is proportional to the difference between the fourth power of the outer diameter and the fourth power of the inner diameter. Thus, increasing the diameter of the core wire 112 or increasing the thickness of hypotube 114 are two ways to increase the total stiffness of the cross section. However, space must still exist for the electrical conductors 107a-e to freely extend without damage. Thus, constraints on outer diameter of the hypotube 114 limit the ability of the prior art designs to improve the stiffness of the guidewire.

Figure 7:
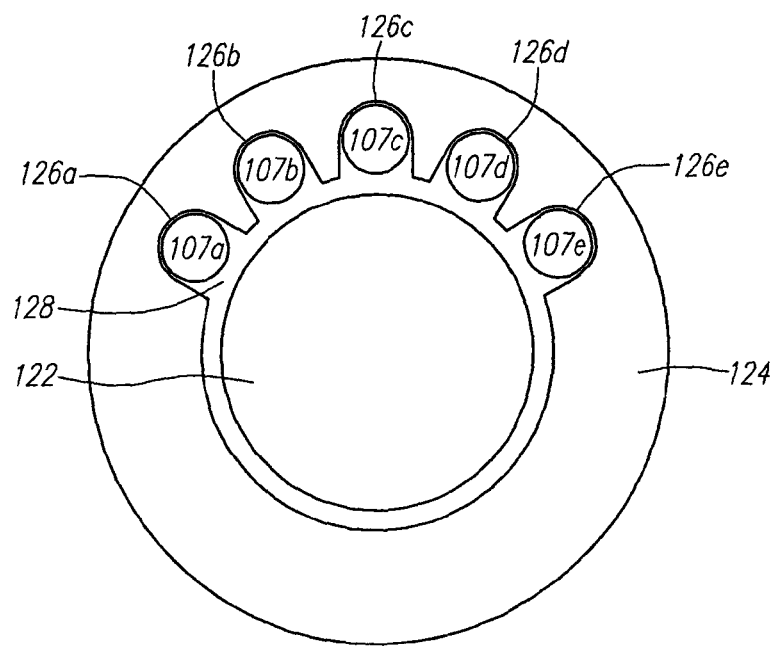
FIG. 7 illustrates a cross-section of an embodiment of the guidewire according to the present invention.

FIG. 7 depicts a guidewire according to the present invention that allows for increased stiffness while still allowing for the electrical conductors to extend freely. Here, the elongate tubular member 124 has thickened walls which further contain a plurality of longitudinal recesses, or grooves, 126a-e disposed on the inner surface and extending the length of the tubular member 124. The wire conductors 107a-e, may then be positioned in the grooves 126a-e where they will still have space to freely extend the length of the cable. Since the conductors 107a-e are resting partially inside the grooves, the wall thickness of the tubular member 124 may be increased without cutting onto the necessary space for the wire conductors 107a-e. In addition, the excess space also allows for the stiff inner core wire 122 to be increased in diameter to further reinforce the stiffness of the guidewire. The remaining space between the conductors 107a-e and the core wire 122 is filled with insulative material 128.

Figure 7A:
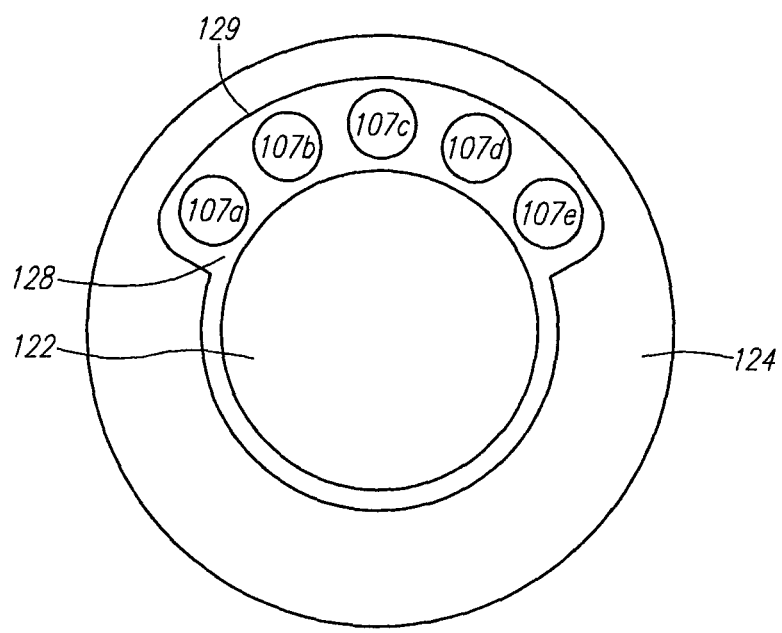
FIG. 7a illustrates a cross-section of an embodiment of the guidewire according to the present invention.

FIG. 7a depicts an alternative embodiment of the improved guidewire. Here, the elongate tubular member 124 has thickened walls which further contain a single longitudinal recess 129, instead of a plurality of recesses, disposed on the inner surface and extending the length of the tubular member 124. The single longitudinal recess 129 is operably sized to house all the conductor wires 107 a-e with enough space to permit them to extend freely the length of the elongate tubular member. The remaining space between the conductors 107a-e themselves and between the conductors 107a-e and the core wire 122 is filled with insulative material 128.

The following table shows an example of the increase in wall thickness of the hypotube and core wire diameter a 0.014" guidewire between the embodiments shown in FIGS. 6 and 7.

|  | FIG. 6 Embodiment | FIG. 7 Embodiment |
| --- | --- | --- |
| Tubular member outer diameter | .014" | .014" |
| Tubular member inner diameter | .010" | .008" |
| Core Wire Diameter | .005" | .007" |
| Electrical conductor diameter | .0015" | .0015" |

The increase in stiffness of the core wire of FIG. 7 is equal to:

$$(0.007")^4/(0.005")^4=3.8$$

Therefore, the core wire 122 of FIG. 7 is 3.8 times stiffer than the core wire 112 of FIG. 6. The increase in stiffness of the tubular member of FIG. 7 is equal to:

$$((0.014")^4-(0.008")^4)/((0.014")^4-(0.010")^4)=1.2$$

Therefore, the tubular member 124 of FIG. 7 is 1.2 times stiffer than the tubular member 114 of FIG. 6, neglecting any minor effect from the groove(s).

In an alternative embodiment (not shown), it is also possible to incorporate only the thickening of the hypotube wall, or only the increase in the core wire diameter. Additionally, if only the wall thickness of the hypotube is increased, and the core wire diameter stays the same, the thickness of the hypotube can be increased even more while still leaving space for the conductor wires and thus the increase of stiffness resulting from the hypotube thickness becomes even greater.

Figure 9:
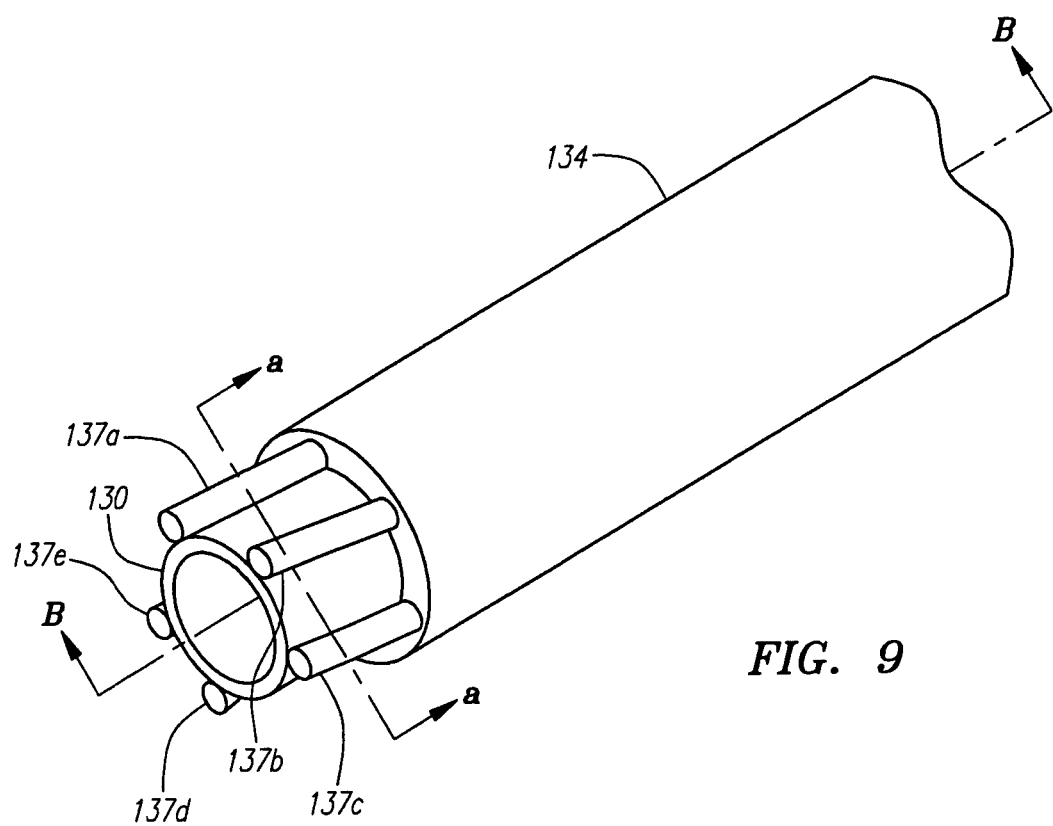
FIG. 9 illustrates an alternative embodiment of the guidewire according to the present invention.
Figure 9A:
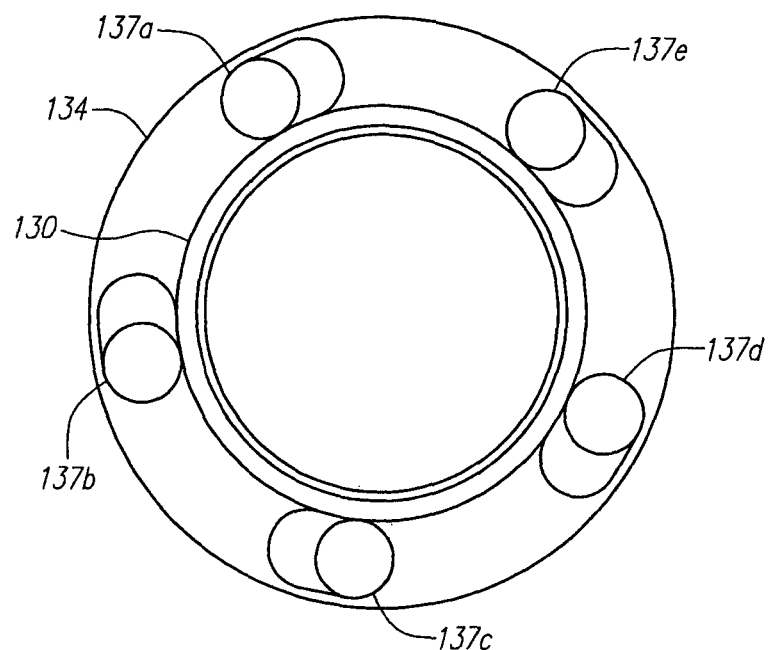
FIG. 9a illustrates a cross-section of the guidewire illustrated in FIG. 9 taken along the line a-a.
Figure 9B:
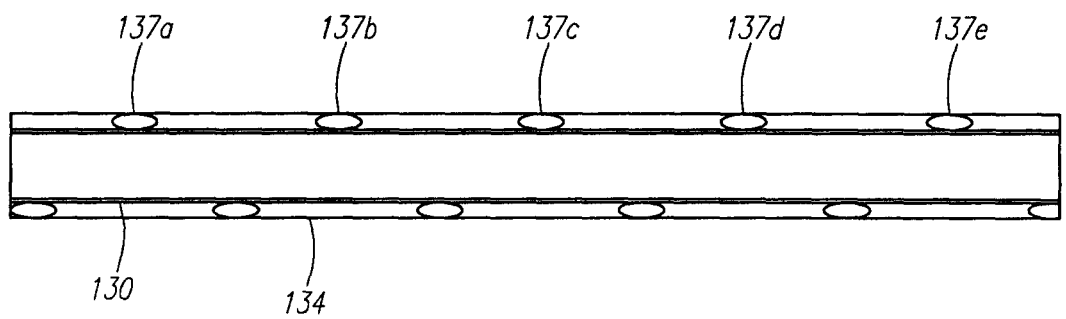
FIG. 9b illustrates a longitudinal section of an alternative embodiment of the guidewire illustrated in FIG. 9 taken along the line B-B.
Figure 12:
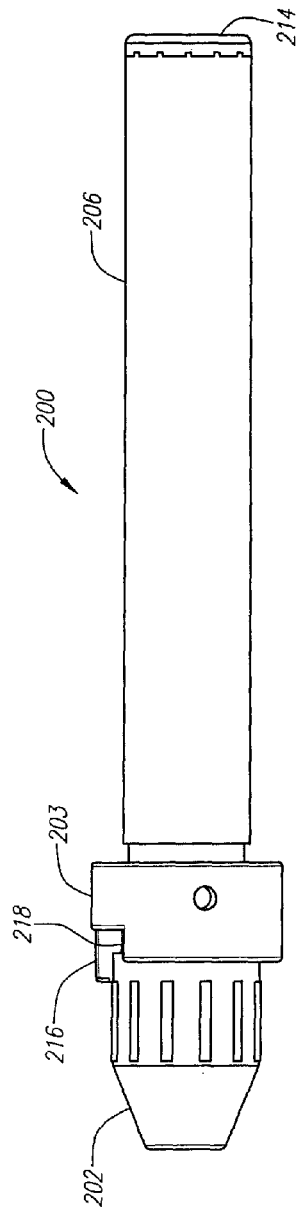
FIG. 12 illustrates an embodiment of the connector of the present invention.

Alternatively, as depicted in FIGS. 8-9b, the guidewire may be created out of a composite polyimide tube wherein the electrical conductor wires 137a-e may be sandwiched between layers of the polyimide tube 130 and 134 as it is being formed. The process for making this tube is shown in FIGS. 8-9b. The first polyimide layer(s) 130 are deposited over a sacrificial mandrel (not shown) whose outer contours are similar to the inner diameter of the hypotube 124 of FIG. 7. FIG. 8 shows five separate insulated wires 137a-e wrapped around the first polymide layer(s) 130. Alternatively, the five wires may be supplied on the same flex circuit. Each of the wires in FIG. 8 has a conductive core 132 made from a conductive material, such as copper and an insulative coating 131 made from an insulative material, such as polyimide, fluoropolymer, PEBAX or other insulative materials. The wires 137a-e are wrapped around the circumference of the tubular form of the first polyimide layer(s) 130. As shown in to FIG. 9, final layer(s) of polyimide 134 are deposited over the first polyimide layer(s) 130 and the electrical conductor wires 137a-e. The resulting composite tube has an inner diameter of, for example, 0.009" and an outer diameter of 0.014". Because the conductive wires are self-contained in the wall of the tube, and insulated from each other and from other metallic components by the polyimide layers, additional insulating material between the electrical conductors and the steel inner core wire is no longer necessary. Thus, in this embodiment, the core wire diameter can now be increased to an even greater extent so that it substantially fills the inner diameter of the composite tube, for example a 0.008" diameter core wire may be placed down the inner diameter of a composite tube with a 0.009" inner diameter.

FIG. 9a shows a cross section of FIG. 9 taken along line a-a. Here, the electrical conductor wires 137a-e are disposed between the polyimide layers 130 and 134. FIG. 9b depicts a longitudinal section of FIG. 9 taken along line B-B, showing the electrical conductor wires 137a-e sandwiched between the polyimide layers 130 and 134 of the tubular elongate member. At distal end of the composite tube 160, the polyimide material is dissected away, and the conductive wires extend to the distal end of the product, where they are attached to the respective sensor, such as the pressure sensor or the ultrasound transducer.

The completion of the proximal end assembly, i.e. the male connector, is shown in FIGS. 10 and 11. In FIG. 10, polyimide material is removed by one of many methods familiar in the art, such as cutting, grinding, etching, ablating, burning and drilling. One preferred method is laser machining. The polyimide is removed at a point 140a-e (d and e not shown) for each of the five wires: for wire 137a at removal point 140a, for wire 137b at removal point 140b, etc.

The termination of the male connector is performed by a metal deposition process at a proximal section 162 of the composite tube 160. An area made up of intermediate areas 150a, 150b, 150c and 150d is masked and metal is deposited at areas 130a, 130b, 130c, 130d and 130e. A process of this nature is described in U.S. Pat. No. 6,210,339, incorporated herein by reference in its entirety. The deposited metal (or any conductive material) permanently adheres or couples to the exposed conductive wires at points 140a-e where the polyimide layers were removed. After the masking material 150a-d is removed, there are five independent conductive stripes 130a-e, each connected to a different respective electric wire. Because of the precision nature of the winding process as well as the masking and metal deposition processes, a male connector is made that is short in length, yet very reliable, in mating with a female connector and cable. Any metallizing process is conceived here, including the metallizing of the entire section 162, followed by the etching of the metal material at 150a, 150b, 150c and 150d. Alternatively, conductive bands may be coupled to the exposed ends of the electric wires instead of the metallizing process.

In use, the combination sensor tip 100 is mounted on the distal extremity of the guidewire. The guide wire with the combination sensor tip 100 mounted thereon may then be used in connection with a patient lying on a table or a bed in a cath lab of a typical hospital in which a catheterization procedure such as for diagnosis or treatment is being performed on the patient. The guide wire may be used with an apparatus, such as a connector, that consists of a cable that connects the guide wire to an interface box. The interface box may be connected by another cable to a control console that has incorporated as a part thereof a video screen on which measurements are displayed, such as, e.g., a waveform displaying ECG measurements as well as representations of the measurements being made by the combination sensor tip 100. The ability to measure and compare both the pressure and velocity flow and create an index of hyperemic stenosis resistance significantly improves the diagnostic accuracy of this ischemic testing. It has been shown that distal pressure and velocity measurements, particularly regarding the pressure drop-velocity relationship such as Fractional Flow reserve (FFR), Coronary flow reserve (CFR) and combined P-V curves, reveal information about the stenosis severity. For example, in use, the guidewire may be advanced to a location on the distal side of the stenosis. The pressure and flow velocity may then be measured at a first flow state. Then, the flow rate may be significantly increased, for example by the use of drugs such as adenosine, and the pressure and flow measured in this second, hyperemic, flow state. The pressure and flow relationships at these two flow states are then compared to assess the severity of the stenosis and provide improved guidance for any coronary interventions. The ability to take the pressure and flow measurements at the same location and same time with the combination tip sensor, improves the accuracy of these pressure-velocity loops and therefore improves the accuracy of the diagnostic information.

FIGS. 12-15 depict an improved connector used to couple the guide wire with a combination sensor tip to a physiology monitor. The connector 200 includes a nosepiece 202 coupled to a connector housing 206, with the nosepiece 202 being located on the distal end of the connector housing 206 and when in use oriented towards the proximal end of a guide wire. A retainer 203 is secured to a threaded shell 204 located on the distal end of the connector housing 206 by means of a setscrew 208. The retainer 203 limits the rotation of the nosepiece 202 during operation between a locked and unlocked position. The connector housing 206 has an inner passage which further contains a stationary contact housing 207 for electrically connecting to the conductors of the coupled guidewire and a rotatable collet/bearing assembly 205 for physically engaging the wire.

Figure 13:
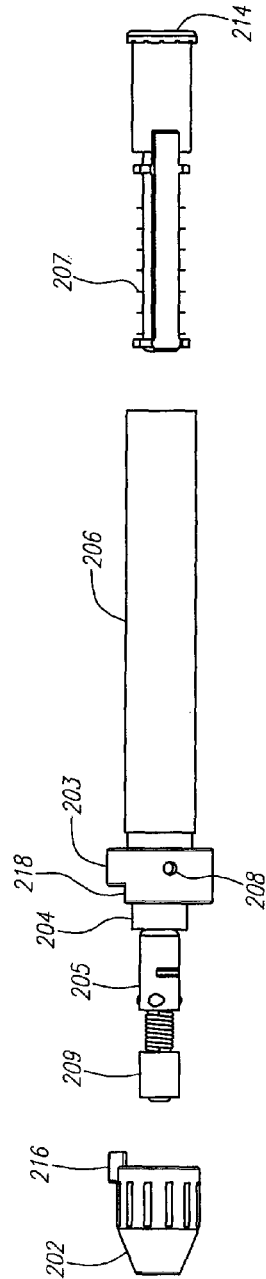
FIG. 13 illustrates an expanded view of the connector of the present invention.
Figure 14:
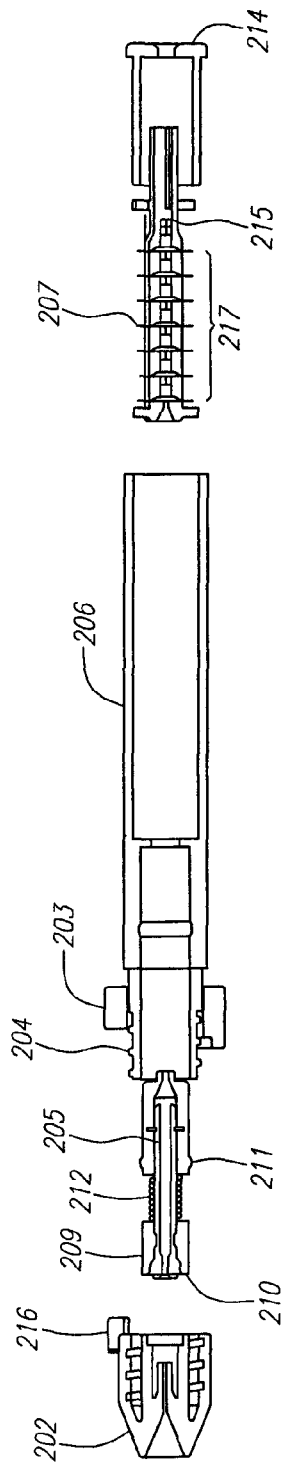
FIG. 14 illustrates a sectional expanded view of the connector of the present invention.
Figure 15:
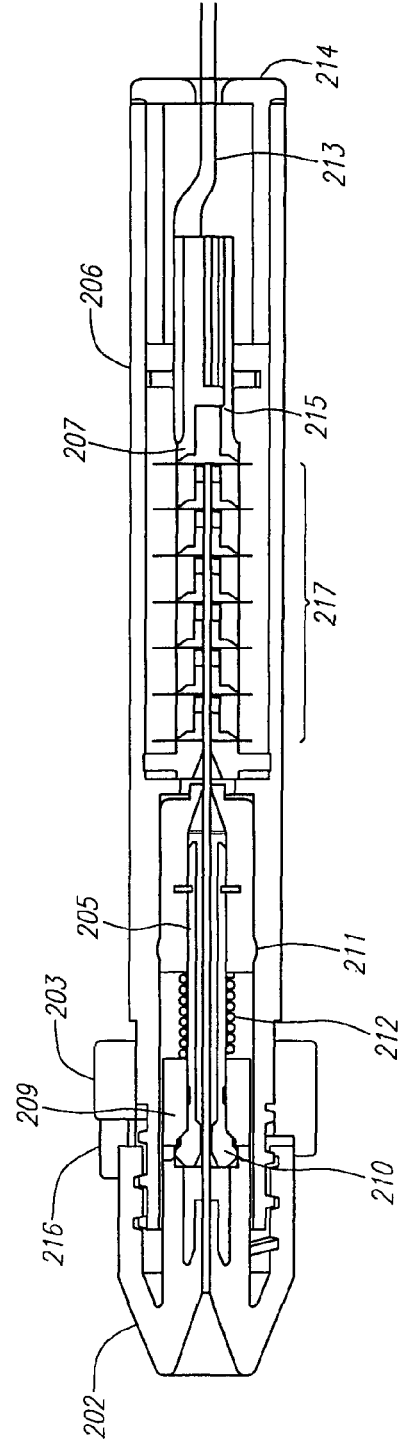
FIG. 15 illustrates an embodiment of the connector of the present invention.

As shown on FIGS. 13-15, the collet/bearing assembly 205 further comprises a collet head 210 which can be shifted between an open and closed position to alternately engage or disengage a guide wire, a spring 212 and collet housing 209 to facilitate shifting the collet head between the open and closed positions and a rotational bearing 211 which permits the collet/bearing assembly to freely rotate within the connector housing 206. As disclosed in U.S. Pat. No. 5,348,481, incorporated herein by reference, the ability of the collet/bearing assembly 205 to freely spin within the connector housing 206 acts to reduce the stress on the guidewire joints during steering and handling of the guide wire. For example, the free spinning nature of the collet/bearing assembly 205 enables a user to maneuver the guide wire with a reduced amount of torque relative to prior art connectors because torsional resistance is reduced as a result of the spinning movement of the collet/bearing assembly 205.

The contact housing 207 is located near the proximal end of the connector 200. The contact housing further contains a plurality of electrical contacts 217 for connecting with the conductive bands on the proximal end of a guidewire. The contact housing 207 does not rotate as the guidewire rotates. In addition, a connector cable 213 extends proximally from the contact housing 207 through an end cap 214 located at the proximal end of the connector 200. The connector cable 213 is configured to be coupled with a cable leading to a physiology monitor.

In use, when the connector 200 is in an unlocked position, the nose piece 202 is pressing down on the collet housing 209 and compressing the spring 212 thus allowing for expansion of the collet head 210 which provides an opening through which the guidewire may pass. As shown in FIG. 16, the guide wire 220 may then be inserted into the connector 200 and passed through the collet/bearing assembly 205 and the multiple contacts 217 of the contact housing 207 until the guidewire touches the backplate 215 of the contact housing 207 and a positive stop is felt. In this position, the conductive bands on the proximal end of the guide wire are lined up with the multiple contacts 217 of the connector housing and are physically in contact with contacts 217 of the contact housing 207.

FIG. 17 depicts a flow guidewire 222 with two conductive bands 227a and 227b located on the proximal end of the guidewire 222. When inserted in the connector 200, the conductive bands 227a and 227b on the flow sensor guidewire 222 make contact with a respective electrical contact 217a and 217b in the contact housing 207. Similarly, FIG. 18 depicts a standalone pressure wire 232 with three conductive bands 237a-b and 238. When inserted in the connector 200, the conductive band 237a makes contact with two electrical contacts 217c-d, the conductive band 237b makes contact with two electrical contacts 217e-f and the conductive contact 238 is grounded via contact with 217g. In FIG. 19, a combined pressure and flow sensor guidewire wherein the flow sensor conductive bands 217a-b are each in contact with a single electrical contact 217a-b in the contact housing and the pressure sensor ground wire 238 is in contact with a single grounded contact 217g, while the pressure sensor conductive bands 237a-b are each in contact with two electrical contacts 217c-d and 217e-f for redundancy. This use of redundant contacts 217c-d and 217e-f for the contact wires 237a-b from the pressure sensor ensures a more reliable electrical contact between the guide wire and the connector 200 is produced because if one dynamic contact fails at any point during rotation of the connector 200 with respect to the contact housing 207, another redundant contact is also connected to assure no lapses.

The guidewire may then be locked into place by turning the nosepiece 202 to the locked position. When the nosepiece is moved to the locked position, the spring 212 in the collet/bearing assembly 205 is released causing the collet housing 209 to compress the collet head 210 and thereby engage the guidewire. Thus, the engaged guidewire will be able to freely rotate with the collet/bearing assembly 205, however the longitudinal position of the guidewire will remain fixed. This ensures that the conductive bands of the guidewire will remain in contact with their respective contacts 217 in the contact housing 207 despite the rotational movement of the guidewire. The alighment of the electrical contacts of the guidewire with at least two contacts in the contact housing further ensures the reliability of electrical connection etween the guidewire and the contacts in the connector.

In one embodiment, turning the nosepiece 202 approximately a quarter turn locks the guide wire in place and turning the nosepiece 202 approximately a quarter turn in the reverse direction unlocks the guide wire from the connector 200. This is achieved by using a left hand (reverse) thread. The reverse direction is used to allow the connector to operate with clockwise attachment and counterclockwise detachment, thus ensuring the motion is intuitive to the user. A stop tab 216 on the nosepiece 202 is configured to contact the locked position 218 on the retainer 203 when the nosepiece 202 is locked, and thereby to provide tactile feedback to the user indicating whether the connector 200 is locked or unlocked. Thus, the connector 200 of the present invention is relatively simple to operate due to the uncomplicated manner of locking and unlocking the guide wire by turning the nosepiece 202 approximately one quarter turn in either of two directions.

Although the foregoing invention has for the purposes of clarity and understanding, been described in some detail by way of illustration and example, many variations and modifications will become apparent to those skilled in the art. It is therefore intended and expected that the certain changes and modifications may be practiced which will still fall within the scope of the appended claims.

What is claimed is:

1. A system for measuring blood pressure and a blood flow characteristic other than blood pressure at a region of interest in a vessel without restricting flow in the vessel, comprising:
    a flexible elongate member having a proximal portion, a distal portion, and an outer diameter less than or equal to 0.018 inches, a sensor housing secured to the distal portion of the elongate member, a pressure sensor, and a sensor for measuring the blood flow characteristic other than blood pressure, wherein the pressure sensor and the sensor for measuring the blood flow characteristic other than blood pressure are positioned within the sensor housing such that the pressure sensor and the sensor for measuring the blood flow characteristic other than blood pressure are less than 3 cm from one another, wherein the sensor housing extends continuously between the pressure sensor and the sensor for measuring the blood flow characteristic other than blood pressure;
    a control console in communication with the pressure sensor and the sensor for measuring the blood flow characteristic other than blood pressure, the control console configured to:
        obtain, from the pressure sensor, a first blood pressure measurement at the region of interest within the vessel in a first flow state;
        obtain, from the pressure sensor, a second blood pressure measurement at the region of interest within the vessel in a second flow state;
        obtain, from the sensor for measuring the blood flow characteristic other than blood pressure, a first blood flow characteristic measurement other than blood pressure in the first flow state;
        obtain, from the sensor for measuring the blood flow characteristic other than blood pressure, a second blood flow characteristic measurement other than blood pressure in the second flow state;
        determine a severity of a stenosis in the region of interest by performing at least one of the following steps:
            comparing the first blood pressure measurement and the second blood pressure measurement; and
            comparing the first blood flow characteristic measurement other than blood pressure and the second blood flow characteristic measurement other than blood pressure.

2. The system of claim 1, wherein the sensor for measuring the blood flow characteristic other than blood pressure is a flow velocity sensor.

3. The system of claim 2, wherein the flow velocity sensor is an ultrasound transducer.

4. The system of claim 2, wherein the flow velocity sensor is a Doppler flow sensor.

5. The system of claim 1, wherein determining the severity of the stenosis includes forming a combined P-V curve based on the first blood pressure measurement, the second blood pressure measurement, the first blood flow characteristic measurement other than blood pressure, and the second blood flow characteristic measurement other than blood pressure.

6. The system of claim 1, wherein determining the severity of the stenosis includes calculating a Fractional Flow Reserve (FFR) based on the first blood pressure measurement and the second blood pressure measurement.

7. The system of claim 1, wherein determining the severity of the stenosis includes calculating a Coronary Flow Reserve (CFR) based on the first blood flow characteristic measurement other than blood pressure and the second blood flow characteristic measurement other than blood pressure.

8. The system of claim 1, wherein the second flow state has an increased flow relative to the first flow state.

9. The system of claim 1, wherein the increased flow of the second flow state results from administering a drug to a patient.

10. The system of claim 1, wherein the first blood pressure measurement and the first blood flow characteristic measurement other than blood pressure are obtained simultaneously.

11. The system of claim 10, wherein the second blood pressure measurement and the second blood flow characteristic measurement other than blood pressure are obtained simultaneously.

12. The system of claim 1, wherein the first blood pressure measurement, the second blood pressure measurement, the first blood flow characteristic measurement other than blood pressure, and the second blood flow characteristic measurement other than blood pressure are obtained distal of the stenosis.

13. The system of claim 9, wherein the control console is configured to obtain the first blood pressure measurement, the second blood pressure measurement, the first blood flow characteristic measurement, and the second blood flow characteristic measurement prior to treatment of the stenosis.

14. The system of claim 1, wherein the control console is configured to output, to a display, a representation of at least one of the first blood pressure measurement, the second blood pressure measurement, the first blood flow characteristic measurement other than blood pressure, or the second blood flow characteristic measurement other than blood pressure.

15. The system of claim 8, wherein the control console is configured to simultaneously obtain the first blood pressure measurement and the first blood flow characteristic measurement other than blood pressure in the first flow state and to simultaneously obtain the second blood pressure measurement and the second blood flow characteristic measurement other than blood pressure in the second flow state.

16. The system of claim 1, wherein the pressure sensor and the sensor for measuring the blood flow characteristic other than blood pressure are positioned in proximity to one another to obtain blood pressure measurements and blood flow characteristic measurements respectively at approximately the same location and approximately the same time.

17. The system of claim 1, wherein the sensor housing is positioned at a distal tip of the distal portion of the flexible elongate member.

18. The system of claim 1, wherein the sensor housing is positioned about 1.5 centimeters to 3.0 centimeters from a distal tip of the distal portion of the flexible elongate member.

19. The system of claim 1, wherein the flexible elongate member further including a radiopaque tip coil having a distal end, the distal end of the radiopaque tip coil being threaded onto a proximal end of the sensor housing.

* * * * *